United States Patent [19]  [11] 4,067,874
Ursprung  [45] Jan. 10, 1978

[54] NOVEL PYRIDINE 1-OXIDES
[75] Inventor: Joseph J. Ursprung, Kalamazoo, Mich.
[73] Assignee: The Upjohn Company, Kalamazoo, Mich.
[21] Appl. No.: 588,749
[22] Filed: June 20, 1975

Related U.S. Application Data
[63] Continuation of Ser. No. 165,723, July 23, 1971, abandoned.

[51] Int. Cl.² ............................................ C07D 401/04
[52] U.S. Cl. .......................... 260/293.69; 260/268 H; 260/296 R; 424/246; 424/248.56; 424/250; 424/263; 424/248.4; 424/267; 260/243.3; 544/60; 544/82; 544/124
[58] Field of Search .................. 260/243 B, 247.5 GP, 260/268 H, 293.69, 296 R, 247.5 G

[56] References Cited
PUBLICATIONS
Ochial, "J. Org. Chem.", 18 pages, 534–551 (1953).
Culvenor, "Amine Oxides", Rev. Pure and Applied Chem. vol. 3, pp. 83–114 (1953).
Anker et al., "J. Chem. Soc.", (1946) pp. 117–120.

*Primary Examiner*—Henry R. Jiles
*Assistant Examiner*—Robert T. Bond
*Attorney, Agent, or Firm*—Martin B. Barancik; Carl A. Randles, Jr.; Roman Saliwanchik

[57] ABSTRACT
Some new 4-amino-2-lower-alkyl-6-variable-pyridine-1-oxides are described. A new process is provided. The 6-variable is lower-alkyl, amino or substituted amino including saturated heterocyclic amino, e.g., pyrrolidinyl, piperidino, etc. The compounds are hypotensive agents and reduce blood pressure in animals.

10 Claims, No Drawings

NOVEL PYRIDINE 1-OXIDES

This is a continuation of pending application Ser. No. 165,723 filed July 23, 1971, now abandoned.

SUMMARY OF THE INVENTION

This invention pertains to new chemical compounds and a process for preparing the same. The invention is more particularly directed to new 4-amino-2-lower-alkyl-6-variable-pyridine-1-oxides, and a process for preparing the same from new 4-halo-2-lower-alkyl-6-variable-pyridine-1-oxide intermediates by reaction with a selected primary or secondary amine.

The new 4-amino-2-lower-alkyl-6-variable-pyridine-1-oxides of this invention have the general structural formula:

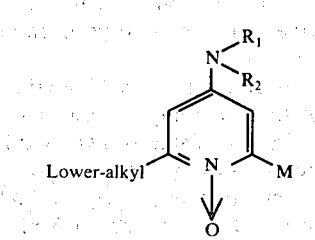

wherein lower-alkyl is of from 1 to 6 carbon atoms, inclusive; M is lower-alkyl, —NH$_2$, or

R$_1$ is hydrogen, lower-alkyl, or lower-alkenyl of from 3 to 6 carbon atoms, inclusive; R$_2$ is lower-alkyl or lower-alkenyl; and further providing that R$_1$ and R$_2$ can be taken together as an alkylene, oxadialkylene, thiadialkylene, or an N-alkylazadialkylene chain thus constituting with the nitrogen atom a saturated heterocyclic amino group of from 5 to 7 ring members, inclusive, the group being optionally lower-alkyl substituted and having a total of not more than 15 carbon atoms. Acid addition salts of the compounds of Formula I constitute a further embodiment of the invention.

The new compounds of this invention, including the acid addition salts, are active in animals as hypotensive agents. They have been found to cause lowering of the blood pressure in normal animals, and can be used therefore to counteract hypertension in animals (including man). In initial screening tests, the specific compounds, 6-amino-4-piperidino-2-picoline-1-oxide, 6-amino-4-(1-pyrrolidinyl)-2-picoline-1-oxide, 6-amino-4-morpholino-2-picoline-1-oxide, and 4-piperidino-2,6-lutidine-1-oxide hemihydrate all caused significant blood pressure lowering in normotensive rats at 4 and 24 hrs. after oral administration of a single 50 mg./kg. dosage. Four rats were used in the tests and the blood pressure lowering was of the order of 4 to 38 mm. of mercury from initial values of 119 to 145 mm. Hg.

DETAILED DESCRIPTION OF THE INVENTION

Having thus briefly described this invention, the following more detailed description of the various embodiments and variables is provided.

The phrase "lower-alkyl is of from 1 to 6 carbon atoms, inclusive;" means methyl, ethyl, propyl, butyl, pentyl, hexyl, and isomeric forms thereof. The phrase "lower-alkenyl of from 3 to 6 carbon atoms, inclusive;" means, for example, allyl, 1-methylallyl, 2-methylallyl (methallyl), 2-butenyl (crotyl), 3-butenyl, 1,2-dimethylallyl, 1,1-dimethylallyl, 1,1-dimethylallyl, 2-ethylallyl, 1-methyl-2-butenyl, 2-methyl-2-butenyl, 3-methyl-2-butenyl, 3-pentenyl, 2,3-di-methyl-2-butenyl, 1,1,2-trimethylallyl, 1,3-dimethyl-2-butenyl, 1-ethyl-2-butenyl, 4-methyl-2-pentenyl, and 4-hexenyl.

The phrase "a saturated heterocyclic amino group of from 5 to 7 ring members" includes, for example, pyrrolidinyl, lower-alkylpyrrolidinyl, for example, 2-methylpyrrolidinyl, 3-butylpyrrolidinyl, and 2-isohexylpyrrolidinyl, polylower-alkylpyrrolidinyl, for example, 2,3-dimethylpyrrolidinyl, 2,2-dimethylpyrrolidinyl, 2,5-diethylpyrrolidinyl, and 2,3,5-trimethylpyrrolidinyl, piperidino, lower-alkylpiperidino, for example, 2-methylpiperidino, 3-methylpiperidino, 4-methylpiperidino, 3-isopropylpiperidino, and 4-tert-butylpiperidino, polylower-alkylpiperidino, for example, 3,4-diethylpiperidino, 2-methyl-5-ethylpiperidino, 3,5-dipentylpiperidino, 2,4,6-trimethylpiperidino, and 2,3,5-triethylpiperidino, hexamethyleneimino, lower-alkyl-hexamethyleneimino, for example, 2-ethylhexamethyleneimino, 4-tert-butylhexamethyleneimino, and 3-heptylhexamethyleneimino, polylower-alkylhexamethyleneimino, for example, 2,4-dimethylhexamethyleneimino, 3,3-dimethylhexamethyleneimino, 2,4,6-tripropylhexamethyleneimino, and 2,2-dibutylhexamethyleneimino, 4-lower-alkylpiperazinyl, for example, 4-methylpiperazinyl and 4-isopropyliperazinyl, polylower-alkylpiperazinyl, for example, 2,2,4,5,5-pentamethylpiperazinyl, and 2,4,5-trimethylpiperazinyl, morpholino, lower-alkylmorpholino, for example, 2-ethylmorpholino and 3-isobutylmorpholino, polylower-alkylmorpholino, for example, 2-ethyl-5-methylmorpholino, 3,3-dimethylmorpholino, and 2,6-di-tert-butylmorpholino, thiamorpholino, lower-alkylthiamorpholino, for example, 3-methylthiamorpholino, and polylower-alkylthiamorpholino, for example, 2,3,6-trimethylthiamorpholino and 2,3,5,6-tetramethylthiamorpholino.

The foregoing specified and many other like saturated heterocyclic amino groups are contemplated as being within the scope of this invention. It will be noted that the saturated amino heterocycle can be other than cycloalkyleneimino and there can be a second hetero atom in the ring, i.e., an oxygen atom, a sulfur atom, or a second nitrogen atom as a ring member. In general, the second hetero atom is preferably in the 4-position of a six-membered ring, but it can be in the 3-position. Accordingly, it will be recognized that the "taken together" concept can be alkylene, oxadialkylene, e.g.,

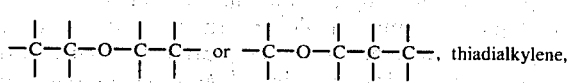

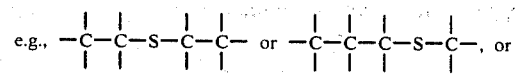

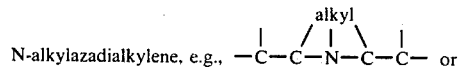

-continued

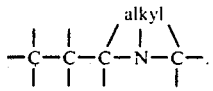

The acid addition salts embodiment of the invention include both mono- and diacid addition salts. Such salts are usually obtained by merely conventional neutralization of a free base compound of the invention with an acid. Otherwise, certain acid addition salts can be obtained by a metathetic reaction involving two interconvertible acid addition salts.

Representative acid addition salts include the mono- and dihydrochlorides (preferred), the hydrobromides, the hydrogen sulfates, the phosphates, nitrates, acetates, propionates, benzoates, palmitates, succinates, gluconates, mucates, citrates, tartrates, pamoates, salicylates, cyclohexylsulfamates, and p-toluenesulfonates.

The 4-amino-2-lower-alkyl-6-variable-pyridine-1-oxides of this invention (compounds according to Formula I, above) are prepared according to the new process of the invention by effecting a displacement of the 4-halogen atom (preferably bromine or chlorine) of a 4-halo-2-lower-alkyl-6-variable-pyridine-2-oxide with an amino group,

For this purpose the amino group is a primary or secondary amine, i.e.,

wherein $R_1$ and $R_2$ are as defined previously.

The 4-halo-2-lower-alkyl-6-variable-pyridine-1-oxide and primary or secondary amine are heated together in the presence of an aqueous reaction medium in order to effect the amino displacement of halogen. Heating is advantageously in the temperature range 125° to 200° C., preferably in the range 140° to 180° C. Water being an essential component of the reaction medium, and since both the water and many of the amine reactants

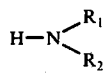

will boil away at the indicated reaction temperatures, the reaction is effected in a sealed, pressure resistant reaction vessel.

For efficiency, at least one molecular equivalent of the displacing amine should be used, but 2 or even more molecular equivalents are usually preferred. An excess of the amine helps provide a homogeneous reaction mixture, and promotes better yields of desired product. Representative suitable amines

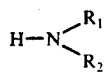

are already indicated.

The desired 4-amino-2-lower-alkyl-6-variable-pyridine-1-oxide products are recovered from the reaction mixture and purified by conventional procedures. In accordance with the embodiments of Examples 1, 2, 3, and 4 hereinafter the reaction mixture is cooled and diluted with water before the products are extracted with an organic solvent. Any excess of a volatile amine reactant can be removed by evaporation, if desired.

Suitable organic solvents for the 4-amino-2-lower-alkyl-6-variable-pyridine-1-oxides of this invention include chloroform (preferred), $MeCl_2$, ethylene dichloride, benzene, and toluene. After the product compounds are in solution in the extractive organic solvent any moisture can be removed by dehydration and then the extractive solvent can be removed by evaporation.

Alternatively, the reaction mixture can be treated with dilute aqueous base in order to convert any hydrohalic acid addition salts to the free base and the free base recovered by chromatographic techniques. The free base can be further purified by crystallization and recrystallization procedures.

The 4-halo-2-lower-alkyl-6-variable-pyridine-1-oxide intermediates of the foregoing described reaction are readily prepared from available 2-lower-alkyl-4-nitro-6-variable-pyridine-1-oxides by reaction with an acyl halide preferably an alkanoyl halide especially, acetyl bromide or chloride. This reaction takes place when a 2-lower-alkyl-4-nitro-6-variable-pyridine-1-oxide is added slowly to an acyl halide and the reaction mixture is then heated at the reflux temperature for an appropriate interval.

The desired 2-lower-alkyl-4-halo-6-variable-pyridine-1-oxide is then recovered and purified by conventional procedures. Illustratively, any volatile acetyl halide or by-products of the reaction can be removed by evaporation and the residue remaining can be purified by precipitation, cyrstallization, or chromatographic procedures.

The starting 2-lower-alkyl-4-nitro-6-variable-pyridine-1-oxides are known in the art or can be prepared according to art-recognized methods. For example, 6-chloro-4-nitro-2-picoline-1-oxide was prepared as described by E. V. Brown, J. Am. Chem. S. 70, p. 3565 (1957). Likewise, the preparation of 4-nitro-2,6-lutidine-1-oxide was described by E. Ochiai, J. Org. Chem. 18 pp. 534–551 (1953).

The following examples are illustrative of the process and products of the present invention but are not to be construed as limiting.

EXAMPLE 1:

Preparation of the compound 2-Amino-6-methyl-4-piperidino-pyridine-1-oxide and its hydrochloride salt Part A: Intermediate,
6-amino-4-nitro-2-picoline-1-oxide A reaction solution consisting of 5.66 g. (0.03 mole) 6-chloro-4-nitro-2-picoline-1-oxide and 100 ml. ethanol was saturated with anhydrous ammonia and sealed in a strong bottle. This reaction mixture was heated and maintained at a temperature in the range of 100° to 105° C. for 21 hrs. The bottle and contents were then cooled and the seal was broken. Crystals had formed. The crystals were collected on a filter and washed with a small amount of cold ethanol. Recrystallization from 95% aqueous ethanol yielded 2.06 g. (41% yield) of 6-amino-4-nitro-2-picoline-1-oxide as yellow needles having a melting point at 221° to 222° C. (with decomposition). When a small sample was mixed with ethanolic ferric chloride a blue solution was obtained.

Analysis: Calc'd for $C_6H_7N_3O_3$: C, 42.61; H, 4.17; N, 24.84. Found: C, 43.42; H, 3.80; N, 23.97.

I.R.: NH: 3440; unsat. CH: 3220, 3170, 3110; C=C/C=N/NH def: 1665, 1645, 1570, $NO_2$: 1535, 1345, C—N: 1220, 1085.

U.V.: (ethanol): 210 (18,350); 235 (11,150); 265 (8,250); 319 (5,100); 390 (4,800).

A solution consisting of 1.69 g. (0.01 mole) 6-amino-4-nitro-2-picoline-1-oxide and 75 ml. methanol was heated to the boiling point and 1 ml. concentrated hydrochloric acid (0.012 mole) was added. After heating the acidified solution until evaporation of the methanol had reduced its volume to about 25 ml., it was cooled to 25° C. Solids separated. The solids were collected on a filter and rinsed on the filter first with cold methanol and then with cold ether. There was thus obtained 1.27 g. of 6amino-4-nitro-2-picoline-1-oxide hydrochloride having a melting point at 188° to 189° C.

Part B: Intermediate
2-Amino-4-chloro-6-methylpyridine-1-oxide hydrochloride

After slowly adding 0.85 g. (0.005 mole) of 6-amino-4-nitro-2-picoline-1-oxide (prepared in Part A, above) to 40.0 ml. acetyl chloride, the intense yellow reaction mixture thus obtained was heated at the reflux temperature until colorless (about 3 hrs.). The excess acetyl chloride and volatile by-products of the reaction were then removed by evaporation under reduced pressure on a rotating evaporator. The solid residue thus obtained was dissolved in a minimal amount of absolute ethanol, and then reprecipitated by adding 400 ml. diethyl ether. This precipitate was collected on a filter as a tan solid. The filter cake was dissolved in about 500 ml. warm acetonitrile and the solution was chilled in order to effect crystallization. After collecting the colorless crystals of 2-amino-4-chloro-6-methylpyridine-1-oxide hydrochloride on a filter, the melting point was 257° C. (with decomposition).

Analysis: Calc'd. for $C_6H_8Cl_2N_2O$: C, 36.95; H, 4.13; Cl, 26.25; N, 14.37. Found: C, 36.73; H, 4.02; Cl, 28.31; N, 14.12.

I.R.: NH/OH: 3300, 3100, amine salt: 2500; C=C/C=N/NH def.: 1640, 1600, 1580, 1595; C—O/C—N: 1185, 1115, 1040; arom. sub. 895, 860, 845.

U.V.: ($H_2O$): 225 (43,600); 252 (7,800); 314 (5,900).

Part C: Objective product,
2-amino-6-methyl-4-piperidino-pyridine-1-oxide

A quantity (1.50 g., 0.0077 mole) of 2-amino-4-chloro-6-methylpyridine-1-oxide hydrochloride (prepared in Part B, above) with 6.0 ml. piperidine, and 10.0 ml. water was sealed in a reinforced bottle and heated in an oil bath at the temperature 155° C. for 3.5 hrs. The aqueous reaction mixture was then cooled to 25° C. and diluted with 50 ml. water. The diluted reaction mixture was then extracted with three 50.0 ml. portions of chloroform. The combined chloroform extracts were treated with charcoal, dried over anhydrous sodium sulfate, filtered, and the chloroform was removed by evaporation under reduced pressure. The solid residue thus obtained was crystallized from acetone to give 0.88 g. (55% yield) of 2-amino-6-methyl-4-piperidinopyridine-1-oxide as off-white needles having a melting point at 260° C. (with decomposition). The crystals sinter at about 250° C.

Analysis: Calc'd. for $C_{11}H_{17}N_3O$: C, 63.74; H, 8.27; N, 20.27. Found: C, 63.60; H, 8.31; N, 20.44.

I.R. NH/OH: 3380, 2900 broad; C=C/NH def./C=N: 1640, 1595, 1555, 1485; C—N/N→O: 1220, 1175; arom. CH: 855, 815.

U.V. ($H_2O$): end absorption; 230 (27,100); 277 (15,900); sh. 305 (5,850). (ethanol): 233 (28,450); 279 (17,600); 311 (5,500). (0.1 N alc. acid): 229 (23,850); 237 (23,950); 287 (17,450). (0.1 N alc. base): 233 (19,150); sl. sh. 250 (13,500); 279 (17,950); 311 (5,600).

N.M.R. ($D_2O$): —$CH_2$—: 94 (singlet, 6H); —$CH_3$: 140 (singlet, 3H); —N—$CH_2$: 191 (broad, 4H); exch. H: 280 (singlet, 2H); arom. H: ca. 360-380 (2H).

Part D: Objective product,
2-amino-6-methyl-4-piperidine-1-oxide hydrochloride

A quantity (2.07 g., 0.01 mole) of 2-amino-6-methyl-4-piperidine-1-oxide is added to 10 ml. of 1N methanolic hydrogen chloride (0.01 mole). The solution is evaporated to dryness to yield 2-amino-6-methyl-4-piperidine-1-oxide hydrochloride.

EXAMPLE 2: Preparation of compound
2-Amino-6-methyl-4-morpholinopyridine-1-oxide A quantity (4.88 g., 0.025 mole) of 2amino-4-chloro-6-methylpyridine-1-oxide hydrochloride (prepared in Part B, Example 1, above) with 20.0 ml. morpholine, and 20.0 ml. water was sealed in a reinforced bottle and heated in an oil bath at the temperature 180° C. for 6 hrs. The aqueous reaction mixture was cooled to 25° C. and then reheated to effect removal of excess morpholine and about one-half the water was removed by evaporation. This concentrate was then diluted with 50 ml. water and extracted with three 50-ml. portions of chloroform. The chloroform extracts were combined, dried over anhydrous sodium sulfate, treated with charcoal, and filtered. The chloroform was removed from the filtrate by evaporation under reduced pressure and the solid residue was triturated with acetone. The insolubles were collected on a filter. Testing via thin layer chromatography showed that there were three components. The components were separated by chromatography on a column of silica gel using a solvent mixture consisting of 1 part methanol and 9 parts methylene chloride. The fractions having the most rapidly moving component were collected and combined. The solvents were removed by evaporation. Chloroformic extraction of the original water-diluted reaction mixture was repeated followed by drying, treating with charcoal, filtration, and removal of chloroform was effected as before. This residue was combined with the residue from the chromatographic separation, and a crystallization and recrystallization from acetonitrile was effected. There was thus obtained 1.40 g. (27% yield) of 2-amino-6-methyl-4-morpholinopyridine-1-oxide as colorless needles having a melting point at 292° C. (with decomposition).

Analysis: Calc'd. for $C_{10}H_{15}N_3O_2$: C, 57.40; H, 7.23; N, 20.08. Found: C, 56.74, 57.55; H, 6.95; N, 20.53.

I.R.: NH/OH: 3360, 3000; C=N/C=C/NH def.: 1640, 1600, 1560; C—O/C—N/N—O: 1220, 1180, 1120; arom. CH: 880, 835.

U.V. (water): 230 (30,650); 273 (15,700); sh 302 (5,400).

N.M.R. ($D_2O$): —$CH_3$: 143 (singlet, 3H); N—$CH_2$: 192 (triplet, 4H); O—$CH_2$: 230 (triplet, 4H); —$NH_2$: 281 (singlet, 2H); arom. H: 366-380 (2H).

EXAMPLE 3: Preparation of the compound 2-Amino-6-methyl-4-pyrrolidinylpyridine-1-oxide A quantity (1.95 g., 0.01 mole) of 2-amino-4-chloro-6-methylpyridine-1-oxide hydrochloride (prepared in Part B, Example 1, above) with 10 ml. pyrrolidine and 10 ml. water was sealed in a reinforced bottle and heated in an oil bath at the temperature 155° C. for 5 hrs. After cooling, this reaction mixture was diluted with water and extracted with three 50-ml. portions of methylene chloride. The methylene chloride extract was dried over anhydrous sodium sulfate, treated with charcoal, and filtered. The methylene chloride was removed from the filtrate by evaporation under reduced pressure, and the residue thus obtained was triturated with acetone and collected on a filter. The solids on the filter were crystallized from about 400 ml. acetonitrile. There was thus obtained 0.98 g. (51% yield) of 2-amino-6-methyl-4-pyrrolidinylpyridine-1-oxide as fine white needles having a melting point at 282° C. (with decomposition). The crystals became pink colored after exposure to light for several days.

Analysis: Calc'd. for $C_{10}H_{15}N_2O$: C, 62.15; H, 7.82; N, 21.75. Found: C, 61.59; H, 7.26; N, 21.92.

I.R.: NH/OH: 3380, 3040; C=N/C=C/NH def.: 1645, 1590, 1550, 1500; C—N/N→O: 1275, 1185, arom. CH: 880, 795.

U.V. ($H_2O$): 229 (26,050); 277 (19,800); sh 305 (5,300).

N.M.R. ($D_2O$): —$CH_2$—: 115 (4H); —$CH_3$: 141 (singlet, 3H); —N—$CH_2$—: 185 (4H); —$NH_2$: 282 (singlet, 2H); arom. H: 338–356 (2H).

EXAMPLE 4: Preparation of the compound 4-Piperidino-2,6-Lutidine-1-oxide hemihydrate

Part A: Intermediate, 4-chloro-2,6-lutidine-1-oxide

Following the procedure of Example 1, Part B, but substituting 4-nitro-2,6-lutidine-1-oxide [as prepared by Ochiai, J. Org. Chem. 18, p. 534 (1953)] for 6-amino-4-nitro-2-picoline-1-oxide, there was prepared 4-chloro-2,6-lutidine-1-oxide hydrochloride.

Part B: Objective compound, 4-piperidino-2,6-lutidine-1-oxide

A quantity (1.94 g., 0.01 mole) of 4-chloro-2,6-lutidine-1-oxide hydrochloride with 6 ml. piperidine, and 10 ml. water were sealed in a reinforced bottle and heated, with stirring, in an oil bath at the temperature 155° to 160° C. for 4½ hrs. After cooling the reaction mixture to 25° C. and diluting it with 25 ml. water, several portions of chloroform were used to extract the objective product. The chloroform extracts were combined, dried over anhydrous sodium sulfate, treated with charcoal, and filtered. The filtrate was pale yellow. The chloroform was removed by evaporation under reduced pressure. The solid residue thus obtained was triturated with technical hexane (Skellysolve B, a mixture of isomeric hexanes having a boiling range between 142° and 156° F.) and then crystallized from about 10 ml. ethyl acetate. There was thus obtained 1.06 g. (50% yield) of 4-piperidino-2,6-lutidine-1-oxide as buff-colored crystals having a melting point at 87° to 90° C.

Analysis: Calc'd. for $C_{12}H_{18}N_2O \cdot \frac{1}{2}H_2O$: C, 66.95; H, 8.90; N, 13.01; $H_2O$, 4.18. Found: C, 66.44; H, 8.75; N, 12.95; $H_2O$, 4.03.

I.R. NH/OH: 3380, 2360; C=N/C=C: 1690, 1635, 1560, 1485; N→O/C—N: 1220, 1125, 1065, 1005; arom. CH: 870, 955, 825.

U.V. (ethanol): 203 (22,550); sl sh 225 (8900); 290 (24,050).

N.M.R. ($D_2O$): —$CH_2$—: 96 (singlet broad, 6H); —$CH_3$: 146 (singlet, 6H); N—$CH_2$: 199 (broad, 4H); exch. H: 283 (singlet, 1H); arom. H: 405 (singlet, 2H).

EXAMPLE 5

Part A

Following the procedure of Example 1, Part A, but substituting separately methylamine, ethylamine, isopropylamine, pentylamine, hexylamine, dimethylamine, diethylamine, dipropylamine, N-methyl-tert-butylamine, N-ethylhexylamine, dihexylamine, allylamine, diallylamine, di-2-butenylamine, di-4-hexenylamine, pyrrolidine, piperidine, morpholine, thiamorpholine, hexamethyleneimine, and 2-methylpyrrolidine for anhydrous ammonia, there were prepared the corresponding 6-methylamino-4-nitro-2-picoline-1-oxide,
6-ethylamino-4-nitro-2-picoline-1-oxide,
6-isopropylamino-4-nitro-2-picoline-1-oxide,
4-nitro-6-pentylamino-2-picoline-1-oxide,
6-hexylamino-4-nitro-2-picoline-1-oxide,
6-dimethylamino-4-nitro-2-picoline-1-oxide,
6-diethylamino-4-nitro-2-picoline-1-oxide,
4-nitro-6-dipropylamino-2-picoline-1-oxide,
6-(methyl-tert-butylamino)-4-nitro-2-picoline-1-oxide,
6-(ethylhexylamino)-4-nitro-2-picoline-1-oxide,
6-dihexylamino-4-nitro-2-picoline-1-oxide,
6-allylamino-4-nitro-2-picoline-1-oxide,
6-diallylamino-4-nitro-2-picoline-1-oxide,
6-di(2-butenyl)amino-4-nitro-2-picoline-1-oxide,
6-di(4-hexenyl)amino-4-nitro-2-picoline-1-oxide,
4-nitro-6-pyrrolidinyl-2-picoline-1-oxide,
4-nitro-6-piperidino-2-picoline-1-oxide,
6-morpholino-4-nitro-2-picoline-1-oxide,
4-nitro-6-thiamorpholino-2-picoline-1-oxide,
6-hexamethyleneimino-4-nitro-2-picoline-1-oxide,
6-(2-methylpyrrolidinyl)-4-nitro-2-picoline-1-oxide, respectively.

Part B

Following the procedure of Example 1, Part B, but substituting separately
6-methylamino-4-nitro-2-picoline-1-oxide,
6-ethylamino-4-nitro-2-picoline-1-oxide,
6-isopropylamino-4-nitro-2-picoline-1-oxide,
4-nitro-6-pentylamino-2-picoline-1-oxide,
6-hexylamino-4-nitro-2-picoline-1-oxide,
6-dimethylamino-4-nitro-2-picoline-1-oxide,
6-diethylamino-4-nitro-2-picoline-1-oxide,
4-nitro-6-dipropylamino-2-picoline-1-oxide,
6-(methyl-tert-butylamino)-4-nitro-2-picoline-1-oxide,
6-(ethylhexylamino)-4-nitro-2-picoline-1-oxide,
6-dihexylamino-4-nitro-2-picoline-1-oxide,
6-allylamino-4-nitro-2-picoline-1-oxide,
6-diallylamino-4-nitro-2-picoline-1-oxide,
6-di(2-butenyl)amino-4-nitro-2-picoline-1-oxide,
6-di(4-hexenyl)amino-4-nitro-2-picoline-1-oxide,
4-nitro-6-pyrrolidinyl-2-picoline-1-oxide,
4-nitro-6-piperidino-2-picoline-1-oxide,
6-morpholino-4-nitro-2-picoline-1-oxide,
4-nitro-6-thiamorpholino-2-picoline-1-oxide,
6-hexamethyleneimino-4-nitro-2-picoline-1-oxide, 6-(2-methylpyrrolidinyl)-4-nitro-2-picoline-1-oxide, for 6-amino-4-nitro-2-picoline-1-oxide, there were prepared the corresponding 6-methylamino-4-chloro-2-picoline-1-oxide hydrochloride,
6-ethylamino-4-chloro-2-picoline-1-oxide hydrochloride,
6-isopropylamino-4-chloro-2-picoline-1-oxide hydrochloride,
4-chloro-6-pentylamino-2-picoline-1-oxide hydrochloride,
6-hexylamino-4-chloro-2-picoline-1-oxide hydrochloride,
6-dimethylamino-4-chloro-2-picoline-1-oxide hydrochloride,
6-diethylamino-4-chloro-2-picoline-1-oxide hydrochloride,
4-chloro-6-dipropylamino-2-picoline-1-oxide hydrochloride,
6-(methyl-tert-butylamino)-4-chloro-2-picoline-1-oxide hydrochloride,
6-(ethylhexylamino)-4-chloro-2-picoline-1-oxide hydrochloride,
6-dihexylamino-4-chloro-2-picoline-1-oxide hydrochloride,
6-allylamino-4-chloro-2-picoline-1-oxide hydrochloride,
6-diallylamino-4-chloro-2-picoline-1-oxide hydrochloride,
6-di(2-butenyl)amino-4-chloro-2-picoline-1-oxide hydrochloride,
6-di(4-hexenyl)amino-4-chloro-2-picoline-1-oxide hydrochloride,
4-chloro-6-pyrrolidinyl-2-picoline-1-oxide hydrochloride,
4-chloro-6-piperidino-2-picoline-1-oxide hydrochloride,
6-morpholino-4-chloro-2-picoline-1-oxide hydrochloride,
4-chloro-6-thiamorpholino-2-picoline-1-oxide hydrochloride,
6-hexamethyleneimino-4-chloro-2-picoline-1-oxide hydrochloride,
6-(2-methylpyrrolidinyl)-4-chloro-2-picoline-1-oxide hydrochloride, respectively Part C Following the procedure of Example 1, Part C, but substituting separately
6-methylamino-4-chloro-2-picoline-1-oxide hydrochloride,
6-ethylamino-4-chloro-2-picoline-1-oxide hydrochloride,
6-isopropylamino-4-chloro-2-picoline-1-oxide hydrochloride,
4-chloro-6-pentylamino-2-picoline-1-oxide hydrochloride,
6-hexylamino-4-chloro-2-picoline-1-oxide hydrochloride,
6-dimethylamino-4-chloro-2-picoline-1-oxide hydrochloride,
6-diethylamino-4-chloro-2-picoline-1-oxide hydrochloride,
4-chloro-6-dipropylamino-2-picoline-1-oxide hydrochloride,
6-(methyl-tert-butylamino)-4-chloro-2-picoline-1-oxide hydrochloride,
6-(ethylhexylamino)-4-chloro-2-picoline-1-oxide hydrochloride,
6-dihexylamino-4-chloro-2-picoline-1-oxide hydrochloride,
6-allylamino-4-chloro-2-picoline-1-oxide hydrochloride,
6-diallylamino-4-chloro-2-picoline-1-oxide hydrochloride,
6-di(2-butenyl)amino-4-chloro-2-picoline-1-oxide hydrochloride,
6-di(4-hexenyl)amino-4-chloro-2-picoline-1-oxide hydrochloride,
4-chloro-6-pyrrolidinyl-2-picoline-1-oxide hydrochloride,
4-chloro-6-piperidino-2-picoline-1-oxide hydrochloride,
6-morpholino-4-chloro-2-picoline-1-oxide hydrochloride,
4-chloro-6-thiamorpholino-2-picoline-1-oxide hydrochloride,
6-hexamethyleneimino-4-chloro-2-picoline-1-oxide hydrochloride,
6-(2-methylpyrrolidinyl)-4-chloro-2-picoline-1-oxide hydrochloride, for 2-amino-4-chloro-6-methylpyridine-1-oxide there were prepared the corresponding
6-methylamino-4-piperidino-2-picoline-1-oxide,
6-ethylamino-4-piperidino-2-picoline-1-oxide,
6-isopropylamino-4-piperidino-2-picoline-1-oxide,
6-pentylamino-4-piperidino-2-picoline-1-oxide,
6-hexylamino-4-piperidino-2-picoline-1-oxide,
6-dimethylamino-4-piperidino-2-picoline-1-oxide,
6-diethylamino-4-piperidino-2-picoline-1-oxide,
4-piperidino-6-dipropylamino-2-picoline-1-oxide,
6-(methyl-tert-butylamino)-4-piperidino-2-picoline-1-oxide,
6-(ethylhexylamino)-4-piperidino-2-picoline-1-oxide,
6-dihexylamino-4-piperidino-2-picoline-1-oxide,
6-allylamino-4-piperidino-2-picoline-1-oxide,
6-diallylamino-4-piperidino-2-picoline-1-oxide,
6-di(2-butenyl)amino-4-piperidino-2-picoline-1-oxide,
6-di(4-hexenyl)amino-4-piperidino-2-picoline-1-oxide,
4-piperidino-6-pyrrolidinyl-2-picoline-1-oxide,
6-dipiperidino-2-picoline-1-oxide,
6-morpholino-4-piperidino-2-picoline-1-oxide,
4-piperidino-6-thiamorpholino-2-picoline-1-oxide,
6-hexamethyleneimino-4-piperidino-2-picoline-1-oxide,
6-(2-methylpyrrolidinyl)-4-piperidino-2-picoline-1-oxide, respectively.

EXAMPLE 6

Part A

Following the procedure of Example 1, Part B, but substituting separately
2-amino-6-ethyl-4-nitropyridine-1-oxide,
2-amino-4-nitro-6-propylpyridine-1-oxide,
2-amino-6-isopropyl-4-nitropyridine-1-oxide,
2-amino-6-butyl-4-nitropyridine-1-oxide,
2-amino-6-tert-butyl-4-nitropyridine-1-oxide,
2-amino-4-nitro-5-pentylpyridine-1-oxide, and
2-amino-6-hexyl-4-nitropyridine-1-oxide for 6-amino-4-nitro-2-picoline-1-oxide, there were prepared the corresponding
2-amino-4-chloro-6-ethylpyridine-1-oxide hydrochloride,
2-amino-4-chloro-6-propylpyridine-1-oxide hydrochloride, 2-amino-4-chloro-6-isopropylpyridine-1-oxide hydrochloride,
2-amino-6-butyl-4-chloropyridine-1-oxide hydrochloride,
2-amino-6-tert-butyl-4-chloropyridine-1-oxide hydrochloride,
2-amino-4-chloro-6-pentylpyridine-1-oxide hydrochloride, and
2-amino-4-chloro-6-hexylpyridine-1-oxide hydrochloride, respectively.

Part B

Following the procedure of Example 2, but substituting separately
2-amino-4-chloro-6-ethylpyridine-1-oxide hydrochloride,
2-amino-4-chloro-6-propylpyridine-1-oxide hydrochloride,
2-amino-4-chloro-6-isopropylpyridine-1-oxide hydrochloride,
2-amino-6-butyl-4-chloropyridine-1-oxide hydrochloride,
2-amino-6-tert-butyl-4-chloropyridine-1-oxide hydrochloride,
2-amino-4-chloro-6-pentylpyridine-1-oxide hydrochloride,
2-amino-4-chloro-6-hexylpyridine-1-oxide hydrochloride,
for 2-amino-4-chloro-6-methylpyridine-1-oxide hydrochloride, there were prepared the corresponding
2-amino-6-ethyl-4-morpholinopyridine-1-oxide,
2-amino-4-morpholino-6-propylpyridine-1-oxide,
2-amino-6-isopropyl-4-morpholinopyridine-1-oxide,
2-amino-6-butyl-4-morpholinopyridine-1-oxide,
2-amino-6-tert-butyl-4-morpholinopyridine-1-oxide,
2-amino-4-morpholino-6-pentylpyridine-1-oxide, and
2-amino-6-hexyl-4-morpholinopyridine-1-oxide, respectively.

EXAMPLE 7

Following the procedure of Example 3, but substituting separately methylamine, ethylamine, isopropylamine pentylamine, hexylamine, dimethylamine, diethylamine, dipropylamine, N-methyl-tert-butylamine, N-ethylhexylamine, dihexylamine, allylamine, diallylamine, di-2-butenylamine, di-4-hexenylamine, thiamorpholine, hexamethyleneimine, and 2-methylpyrrolidine for pyrrolidine, there were prepared the corresponding
2-amino-4-methylamino-6-methylpyridine-1-oxide,
2-amino-4-ethylamino-6-methylpyridine-1-oxide,
2-amino-4-isopropylamino-6-methylpyridine-1-oxide,
2-amino-6-methyl-4-pentylaminopyridine-1-oxide,
2-amino-4-hexylamino-6-methylpyridine-1-oxide,
2-amino-6-methyl-4-dimethylaminopyridine-1-oxide,
2-amino-6-methyl-4-dimethylaminopyridine-1-oxide,
2-amino-6-methyl-4-dipropylaminopyridine-1-oxide,
2-amino-6-methyl-4-methyl-tert-butylaminopyridine-1-oxide,
2-amino-4-ethyl-hexylamino-6-methylpyridine-1-oxide,
2-amino-4-di-hexylamino-6-methylpyridine-1-oxide,
2-amino-6-methyl-4-thiamorpholinopyridine-1-oxide,
2-amino-4-hexamethyleneimino-6-methylpyridine-1-oxide,
and 2-amino-4-methylpyrrolidinyl-6-methylpyridine-1-oxide, respectively.

The useful hypotensive activity of the compounds of this invention is not restricted to the oral route of administration herein before described. The compounds or appropriate formulations of the compounds can be administered parenterally also. Topical application techniques are not ruled out, e.g., nasal inhalation.

Solid and fluid dosage forms are contemplated. Solid forms include, for example, tablets, pills, capsules, granules, powders, wafers, cachets, suppositories, boluses, and the like. Fluid forms include, for example, solutions, suspensions, syrups, elixirs, and emulsions.

The solid forms comprise, in general, one or more active compounds according to Formula I and a physiologically acceptable, solid accessory material. Appropriate physiologically acceptable solid accessory materials include corn starch, lactose, dicalcium phosphate, terra alba (calcium sulfate), talc, stearic acid, magnesium stearate, and various synthetic and naturally occurring gums and waxes. Accessory materials including formulation adjuvants such as surfactants or wetting agents, sweetening agents, preservatives, buffers, flavoring and lubricating agents can also be incorporated in solid dosage forms. In general, representatives of the foregoing adjuvants are well known to those skilled in the art of pharmacy and specific enumeration will be avoided for the objective of conciseness.

The fluid forms comprise, in general, one or more active compounds according to Formula I and a physiologically acceptable fluid accessory material, with or without some relatively minor solid components that do not interfere with the fluid-flow characteristic of the formulations. Thus conceptually, the fluid dosage embrace suspensions of finely divided solids in a liquid for oral administration voluntarily, oral intubation, and for injection. Injectable fluid forms can be administered intramuscularly, intravenously, subcutaneously, or intraperitoneally.

Advantageously, fluid dosage forms comprise the active compounds with water, physiological saline, physiologically acceptable oils, and water-oil emulsions. If desired, suitable dispersing or suspending agents can be included, for example, tragacanth, acacia, alginates, dextran, sodium carboxymethylcellulose, methylcellulose, polyvinyl pyrrolidone, gelatine, and mixtures thereof. Suitable oils for solutions and water-oil emulsions include cottonseed oil, sesame oil, coconut oil, and peanut oil.

For parenteral administration further, the 4-amino-2-lower-alkyl-6-variable-pyridine-1-oxides can be formulated in dilute aqueous solutions, aqueous suspensions, and oil dispersions for intramuscular injection, intravenous drip, vascular perfusion, or like routes. Advantageously, a solubilizer, for example N,N-dimethylacetamide (preferred), N,N-dimethylformamide, ethanol, and the like can be utilized. If desired, other aqueous media such as water for injection, normal saline solution, Ringer's solution, blood plasma, and whole blood can be used.

The dosage of 4-amino-2-lower-alkyl-6-variable-pyridine-1-oxides required for a physiological, hypotensive response has not been precisely determined. Dependent variables include, the degree of hypotensive action desired for a particular animal patient, the patient's age, sex, and physical condition, as well as frequency and route of administration. Contemplated is a dosage range of from 0.1 to 50.0 mg. per kg. of body weight. A preferred dosage range is contemplated to be 5 to 25 mg. per kg. of body weight. A daily dosage for a reasonably normal adult human is contemplated at 300 to 1500 mg. Such a dosage can be scheduled as a single dose, multiple divided dosages, or sequential dosages. Accord-

I claim:
1. A compound of the formula

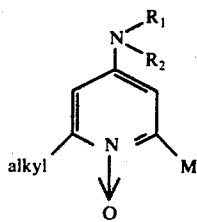

wherein alkyl is from one to six carbon atoms, inclusive; M is alkyl from one to six carbon atoms, inclusive;

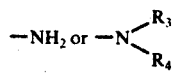

wherein $R_3$ is hydrogen, alkyl of one to six carbon atoms, inclusive, or alkenyl of from three to six carbon atoms, inclusive, and $R_4$ is alkyl of one to six carbon atoms, inclusive or alkenyl of three to six carbon atoms, inclusive, and $R_3$ and $R_4$ taken together are alkylene of five to seven carbon atoms, inclusive, said alkylene unsubstituted or substituted with one or more alkyl groups having one to six carbon atoms, inclusive, the total number of carbon atoms in the ring and alkyl groups not to exceed fifteen, morpholino, thiamorpholino and N-alkyl piperazino, said alkyl having one to three carbon atoms, inclusive; $R_1$ and $R_2$ taken together with the nitrogen atom to which they are attached are pyrrolidino, piperidino or hexamethyleneimino; and an acid addition salt thereof.

2. A compound in accordance with claim 1 wherein $R_3$ is hydrogen, alkyl of one to six carbon atoms, inclusive, alkenyl of three to six carbon atoms, inclusive, $R_4$ is alkyl of one to six carbon atoms, inclusive, or alkenyl of three to six carbon atoms, inclusive; and $R_3$ and $R_4$ taken together with the nitrogen atom to which they are attached are pyrrolidino, piperidino, hexamethyleneimino, morpholino, thiamorpholino, or N-alkylpiperazino wherein alkyl is one to three carbon atoms, inclusive.

3. A compound in accordance with claim 1 wherein M is $NH_2$.

4. A compound in accordance with claim 3 wherein alkyl is methyl.

5. 2-Amino-6-methyl-4-pyrrolidinylpyridine-1-oxide according to claim 4.

6. 2-Amino-6-methyl-4-piperidinylpyridine-1-oxide according to claim 4.

7. A compound according to claim 1 wherein M is alkyl of one to six carbon atoms, inclusive.

8. A compound according to claim 7 wherein M is methyl.

9. A compound according to claim 8 wherein alkyl is methyl.

10. 4-Piperidino-2,6-lutidine-1-oxide according to claim 9.

* * * * *